(12) United States Patent
Winston et al.

(10) Patent No.: US 6,303,104 B1
(45) Date of Patent: Oct. 16, 2001

(54) REMINERALIZING/MINERALIZING ORAL PRODUCTS HAVING IMPROVED WHITENING AND STAIN REMOVAL PROPERTIES

(75) Inventors: Anthony E. Winston; Jordan Barth, both of East Brunswick; Norman Usen, Marlboro, all of NJ (US)

(73) Assignee: Enamelon, Inc., Princeton, NJ (US)

( * ) Notice: Subject to any disclaimer, the term of this patent is extended or adjusted under 35 U.S.C. 154(b) by 0 days.

(21) Appl. No.: 09/249,295

(22) Filed: Feb. 12, 1999

(51) Int. Cl.⁷ .............................. A61K 7/16; A61K 7/18
(52) U.S. Cl. ................................... 424/49; 424/52
(58) Field of Search .......................... 424/49–58

(56) References Cited

U.S. PATENT DOCUMENTS

| | | | |
|---|---|---|---|
| 3,850,683 | * 11/1974 | Hill ..................... | 117/147 |
| 4,080,440 | 3/1978 | DiGiulio et al. ........ | 424/49 |
| 4,083,955 | 4/1978 | Grabenstetter et al. ... | 424/49 |
| 4,177,258 | 12/1979 | Gaffar et al. .......... | 424/52 |
| 4,183,915 | 1/1980 | Gaffar et al. .......... | 424/52 |
| 4,289,753 | 9/1981 | Dyroff et al. .......... | 424/48 |
| 4,348,381 | 9/1982 | Gaffar et al. .......... | 424/52 |
| 4,397,837 | 8/1983 | Raaf et al. ............ | 424/51 |
| 4,568,540 | * 2/1986 | Asano et al. .......... | 424/52 |
| 4,606,912 | 8/1986 | Rudy et al. ........... | 424/52 |
| 4,610,873 | 9/1986 | Rudy et al. ........... | 424/52 |
| 4,664,906 | 5/1987 | Sipos ................. | 424/49 |
| 4,814,163 | * 3/1989 | Barth ................. | 424/49 |
| 4,902,497 | 2/1990 | Crisanti et al. ....... | 424/52 |
| 4,992,259 | * 2/1991 | Schiraldi et al. ...... | 424/49 |
| 5,004,597 | 4/1991 | Majeti et al. ......... | 424/52 |
| 5,037,639 | 8/1991 | Tung ................. | 424/57 |
| 5,041,280 | 8/1991 | Smigel ............... | 424/53 |
| 5,145,666 | 9/1992 | Lukacovic et al. ..... | 424/52 |
| 5,171,564 | 12/1992 | Nathoo et al. ........ | 424/53 |
| 5,213,790 | * 5/1993 | Lukacovic et al. ..... | 424/52 |
| 5,256,402 | 10/1993 | Prencipe et al. ...... | 424/53 |
| 5,268,167 | 12/1993 | Tung ................. | 424/52 |
| 5,279,816 | 1/1994 | Church et al. ........ | 424/53 |
| 5,281,410 | 1/1994 | Lukacovic et al. ..... | 424/52 |
| 5,281,411 | * 1/1994 | Majeti et al. ......... | 424/52 |
| 5,338,537 | * 8/1994 | White et al. ......... | 424/52 |
| 5,401,495 | 3/1995 | Murayama ........... | 424/49 |
| 5,427,768 | 6/1995 | Tung ................. | 424/52 |
| 5,437,857 | 8/1995 | Tung ................. | 424/52 |
| 5,460,803 | 10/1995 | Tung ................. | 424/57 |
| 5,571,502 | 11/1996 | Winston et al. ....... | 424/52 |
| 5,603,922 | 2/1997 | Winston et al. ....... | 424/49 |
| 5,605,675 | 2/1997 | Usen et al. .......... | 424/49 |
| 5,605,677 | 2/1997 | Schumann et al. ..... | 424/52 |
| 5,614,175 | 3/1997 | Winston et al. ....... | 424/52 |
| 5,645,853 | 7/1997 | Winston et al. ....... | 424/440 |
| 5,713,738 | 2/1998 | Yarborough .......... | 433/215 |
| 5,804,172 | * 9/1998 | Ault ................. | 424/70.1 |
| 5,814,304 | 9/1998 | Wong et al. .......... | 424/53 |

FOREIGN PATENT DOCUMENTS

| | | | |
|---|---|---|---|
| 311259 | * | 4/1989 | (EP) . |
| 2108827 | * | 5/1972 | (FR) . |
| 2547832 | * | 12/1984 | (FR) . |
| 2210264 | * | 6/1989 | (GB) . |
| 97 15277 | * | 5/1997 | (WO) . |
| 98 17237 | * | 4/1998 | (WO) . |
| 99 20238 | * | 4/1999 | (WO) . |

OTHER PUBLICATIONS

Abstracts of French Patent 2547 832 Morgan et al. solid surface cleanser with sodium gluconate 10 sodium bicarbonate 30 calcium carbonate 30 1984.*
French Patent 2108827 Cerro sodium glucol losed detact auiza denture, 1972.*
Chinese Patent 85106306A Giao past calcuim gyuconte and sodium gyucone,1990.*
British Patent 2216003 Crisanth sodium gluconte and calcium carbonate US.4902497, 1990.*

* cited by examiner

*Primary Examiner*—Shep K. Rose
(74) *Attorney, Agent, or Firm*—Stuart D. Frenkel; Liniak, Berenato, Longacre & White

(57) ABSTRACT

An oral product, preferably a toothpaste, effective for remineralizing subsurface dental lesions, mineralizing exposed dentinal tubules and whitening teeth stained with discoloring residues containing heavy metal ions such as $Fe^{+3}$, $Mn^{+2}$ and $Cu^{+2}$, is composed of a first discrete part composed of a water-soluble or partially water-soluble calcium salt and optionally a non-toxic, non-calcium water-soluble divalent metal salt, and a second discrete part composed of a water-soluble orthophosphate salt and preferably a water-soluble fluoride salt. Further enhanced stain-removing properties without excessive abrasivity are imparted to the oral product when part (A) further contains an effective amount of an anhydrous dicalcium phosphate abrasive and part (B) further contains an effective amount of a silica abrasive.

20 Claims, No Drawings

REMINERALIZING/MINERALIZING ORAL PRODUCTS HAVING IMPROVED WHITENING AND STAIN REMOVAL PROPERTIES

BACKGROUND OF THE INVENTION

This invention relates to oral products. More particularly, this invention relates to oral products capable of remineralizing subsurface dental lesions and mineralizing exposed dentinal tubules and having improved whitening and stain removal properties.

Remineralizing/mineralizing products have been developed to overcome the damage caused by dental caries, i.e., tooth decay, which is a leading cause of tooth damage in humans. Dental caries usually begins with lesions, which are demineralized areas below the surface of intact dental enamel. These lesions are sometimes visible as "white spots" on the surface of the enamel. If unchecked, enamel within and above a subsurface lesion eventually collapses, leading to cavitation and subsequent loss of tooth structure.

Oral products designed to remineralize subsurface lesions in teeth and mineralize exposed dentinal tubules, i.e., remineralizing/mineralizing products, are disclosed, for example, to U.S. Pat. No. 4,080,440 (DiGiulio et al.); U.S. Pat. Nos. 4,177,258, 4,183,915 and 4,348,381 (all to Gaffar et al.); U.S. Pat. No. 4,083,955 (Grabenstetter et al.); U.S. Pat. No. 4,397,837 (Raaf et al.); U.S. Pat. Nos. 4,606,912 and 4,610,873 (both to Rudy et al.); U.S. Pat. Nos. 5,037,639, 5,268,167, 5,437,857, 5,427,768 and 5,460,803 (all to Tung); U.S. Pat. No. 5,605,677 (Schumann et al.); U.S Pat. No. 5,603,922 (Winston et al.); U.S. Pat. No. 5,605,675 (Usen et al.); U.S. Pat No. 5,571,502 (Winston et al.); U.S. Pat. No. 5,614,175 (Winston et al.); and U.S. Pat. No. 5,645,853 (Winston et al.).

Remineralization can only occur when the tooth structure is still basically intact before a cavity is formed.

In the remineralizing/mineralizing oral products disclosed in the above-cited references, remineralization and mineralization are achieved by increasing the calcium and phosphate ion content in the oral cavity. This is because the primary component of the enamel and dentin in teeth is calcium phosphate in the form of calcium hydroxyapatite.

However, the addition of calcium and phosphate ions in an effective form by dentifrices is not a simple matter. Calcium ions are rather reactive with the conventional ingredients for these products, and can lose their effectiveness virtually entirely by being chemically combined with such ingredients. For example, calcium cannot just be added to dentifrices in the presence of phosphate ions because the two will react with each other to form an insoluble calcium phosphate, which is not effective. By the same token, calcium ions cannot just be combined with fluoride ions because of the precipitation of calcium fluoride, which is also ineffective.

Thus, in the oral products disclosed in the references cited above, premature reaction between the calcium, phosphate and fluoride salts is avoided by keeping the calcium salt physically separate from the phosphate and fluoride salts, by disposing either or both of the cationic and anionic parts in a non-aqueous medium, or by adding a stabilizing agent (e.g., chelating agent, antinucleation agent or water-soluble, non-calcium divalent metal salt) to the product.

Another dental concern for many people is the whiteness of their teeth. For a variety of reasons, it has become desirable for a person's teeth to appear bright or "white".

Society places a high value on the "whiteness" of one's teeth. One whose teeth are white may enjoy more personal confidence and satisfaction and may even enjoy greater social acceptance.

A tooth is composed of an inner dentin layer and an outer hard enamel layer that is the protective layer of the tooth. The enamel layer of a tooth is naturally an opaque white or slightly off-white color. While the dentin below the enamel can sometimes be stained for systemic reasons, such as ingestion of tetracycline while teeth are forming, often it is the enamel layer that can become stained or discolored due to extrinsic deposits in the pellicle. Also, the enamel layer of a tooth is composed of hydroxyapatite mineral crystals that create a somewhat porous surface. As a result, the surface of the enamel layer presents microscopic spaces or pores. The porous nature of the enamel layer can allow staining agents and discoloring substances to permeate the enamel and discolor the tooth.

Many substances that a person confronts or comes in contact with on a daily basis can "stain" or reduce the "whiteness" of the teeth. In particular, colored residues from foods, tobacco products, and fluids that one consumes tend to accumulate in the pellicle layer over the teeth. These staining and discoloring substances can permeate the enamel layer. This problem usually occurs gradually between visits to the dentist, but imparts a noticeable discoloration of the enamel of the teeth. Often, surface stains are removed when the dentist performs a prophy. However, more aggressive treatment is sometimes required. As long as the discolored teeth are still healthy and do not pose any health risk or problem, a product or substance that would whiten the discolored teeth would be advantageous. Such a product would maintain the whiteness of teeth between visits to the dentist.

Oral products for whitening and/or removing stains from teeth are known in the art. Reference is made, for example, to U.S. Pat. No. 5,256,402 (Prencipe et al.), U.S. Pat. No. 5,713,738 (Yarborough), U.S. Pat. No. 5,401,495 (Murayama), U.S. Pat. No. 5,171,564 (Nathoo et al.), U.S. Pat. No. 5,041,280 (Smigel), U.S. Pat. No. 5,814,304 (Wong et al.), and U.S. Pat. No. 5,279,816 (Church et al.). Oral products which are said to reduce plaque and gingivitis with reduced staining are also known. Reference is made, for example, to U.S. Pat. Nos. 5,145,666 and 5,281,410 (both to Lukacovic et al.). Calculus-inhibiting compositions are disclosed, for example, in U.S. Pat. No. 4,289,753 (Dyroff et al.).

Many discoloring residues found on the teeth contain heavy metal ions such as iron, copper and manganese. For example, lipstick residues on the teeth contain iron ions. One way to improve whiteness and remove stains is to use a chelating agent for these metal ions. For example, U.S. Pat. No. 5,713,738 to Yarborough teaches that the use of sodium silicate as a thickener therein is beneficial because of its affinity for iron and other heavy metals. U.S. Pat. No. 5,256,402 to Prencipe et al. teaches the use of chelating agents to stabilize peroxide-containing compositions by chelating metal ions such as $Fe^{+3}$, $Mn^{+2}$ and $Cu^{+2}$. Examples of these chelating agents include the salts of ethylene diamine tetraacetic acid, diethylene triamine pentaacetic acid, phosphonates such as Dequest® (available from Monsanto Chemical Company), and azacycloheptane 2', 2' diphosphonate. In its background section, U.S. Pat. No. 4,289,753 to Dyroff et al. states that French Pat. No. 2,108,827 (published May 26, 1972) teaches that the calcium ion-sequestering capability of sodium gluconate can be used to remove tartar from teeth. Other patents teaching the use of sodium gluconate as an additive (not as chelating agents for calcium ions or heavy metal ions) include, e.g., U.S. Pat. Nos. 4,568,540; 4,664,906; 4,814,163; 4,902,497; 4,992,259; 5,004,597; 5,145,666; 5,281,410; 5,281,411; and 5,338,537.

It would be desirable to provide a single oral product which is capable of remineralizing subsurface lesions in teeth and mineralizing exposed dentinal tubules and of whitening teeth. In particular, it would be desirable to provide a single oral product which is capable of remineralizing subsurface lesions in teeth and mineralizing exposed dentinal tubules and of whitening teeth, wherein whitening is achieved by means of a chelating agent for heavy metal ions. However, this is not a simple matter because of the reactivity of the calcium ions. In other words, the chelating agent which is used to improve whitening must chelate the heavy metal ions but not the calcium ions which are needed to effect remineralization and mineralization.

Thus, it is desirable to improve the whiteness properties of a remineralizing/mineralizing oral product without adversely affecting the remineralizing and mineralizing properties.

A primary object of this invention is to provide a single oral product having both remineralizing/mineralizing properties and whitening (stain-removal) properties.

A further object of this invention is to improve the whitening (stain-removal) properties of a remineralizing/mineralizing oral product without adversely affecting the remineralizing and mineralizing properties.

Another object of this invention is to provide a remineralizing/mineralizing oral product having improved whitening and stain-removing properties but which does not excessively abrade the teeth.

A further object of this invention is to provide an oral product having the aforementioned properties, wherein the product is easy to use by consumers and does not differ significantly in flavor and appearance from customary oral products.

These and other objects which are achieved according to the present invention can be readily discerned from the following description.

SUMMARY OF THE INVENTION

The present invention is based on the discovery that the whitening properties of a remineralizing/mineralizing oral product composed of a water-soluble or partially water-soluble calcium salt and a water-soluble orthophosphate salt will be improved by the addition thereto of sodium gluconate. More particularly, the present invention is based on the discovery that sodium gluconate will chelate heavy metal ions (e.g., iron) found in some discoloring agents on the teeth but will not chelate the calcium ions in the remineralizing/mineralizing product. Thus, the sodium gluconate helps to remove the discoloring substances and stains caused thereby without adversely affecting the remineralizing/mineralizing properties of the oral product.

The present invention is further based on the discovery that the use of anhydrous dicalcium phosphate and a silica abrasive in the oral product of this invention further improves the stain removal properties of the product without excessive abrasion to the teeth.

Thus, the present invention provides an oral product effective for remineralizing subsurface dental lesions and mineralizing exposed dentinal tubules and further capable of whitening teeth stained with discoloring residues containing heavy metal ions, wherein the oral product is composed of:

(A) a first discrete part containing an effective amount of at least one water-soluble or partially water-soluble calcium salt, and (B) a second discrete part containing an effective amount of at least one water-soluble orthophosphate salt, an effective amount of sodium gluconate, and preferably an effective amount of at least one water-soluble fluoride salt; wherein parts (A) and (B) have a pH in water such that a mixed aqueous solution formed by mixing parts (A) and (B) with water and/or saliva has a pH of from about 4.0 to about 10.0.

The first discrete part (i.e., the "cationic" part) may further contain an effective amount of a non-toxic, non-calcium water-soluble divalent metal salt.

In particularly preferred embodiments of the product of this invention, the cationic part further contains anhydrous dicalcium phosphate and the second discrete part (i.e., the "anionic part") further contains a silica abrasive. As stated above, these two components increase the stain-removal properties of the oral product without excessively abrading the teeth.

DETAILED DESCRIPTION OF THE INVENTION

As stated above, the present invention is directed to an oral product having whitening and stain-removal properties in addition to remineralizing and mineralizing properties. The oral product of this invention is particularly capable of removing stains composed of discoloring residues containing heavy metal ions such as, e.g., $Fe^{+3}$, $Mn^{+2}$ and $Cu^{+2}$.

As used herein, the term "oral product" means a product which remains in the mouth for a relatively short period of time, during which time the product is intimately contacted with substantially all surfaces of the teeth, and is then removed. Examples of oral products include toothpastes, prophylactic pastes, tooth polishes, gels, professional gels, and the like.

The term "remineralizing/mineralizing" with respect to the oral product of this invention refers to its ability to remineralize subsurface lesions in teeth and to mineralize exposed dentinal tubules.

The oral product of this invention is composed of two discrete parts, i.e., the cationic part and the anionic part. The cationic and anionic parts are kept separate from one another until the product is to be used. In other words, the cationic and anionic parts coexist in the oral product of this invention in an unmixed state with respect to one another. Alternatively, the cationic and anionic parts can be prevented from reacting on storage by supplying them in an anhydrous mixture.

The cationic part contains at least one water-soluble or partially water-soluble calcium salt and, optionally, a non-toxic, non-calcium, divalent metal salt. The anionic part contains sodium gluconate, at least one water-soluble orthophosphate salt, and preferably at least one water-soluble fluoride salt. In a particularly preferred embodiment of the product of this invention, the first part further contains an anhydrous dicalcium phosphate and the second part further contains a silica abrasive.

As used herein with respect to the calcium salt(s), the term "water-soluble" refers to a solubility in water such that the salt is capable of releasing at least about 1400 ppm by weight of ions into an aqueous solution having a temperature of about 25° C. and a pH of about 7.0.

As used herein with respect to the calcium salt, the term "partially water-soluble" refers to a calcium salt having a solubility which is greater than that of dicalcium phosphate dihydrate in an aqueous solution having a pH of about 7.0 and a temperature of about 25° C. but which is less than that solubility which would release more than about 1400 ppm of calcium cations in such aqueous solution. In an aqueous solution having a pH of about 7.0 at a temperature of about 25° C., dicalcium phosphate dihydrate generally releases about 40 ppm of calcium cations. Thus, the calcium salt used in the present invention generally has a solubility such that the salt is capable of releasing more than about 40 ppm but no more than about 1400 ppm of calcium cations in an aqueous solution having a pH of about 7.0 at a temperature of about 25° C. Preferably, the calcium salt(s) used in this invention has a solubility in such aqueous solution such that the salt(s) releases from about 100 ppm to no more than about 1400 ppm of calcium cations.

With respect to the orthophosphate, fluoride and non-calcium divalent metal salts, the term "water-soluble" refers to a solubility such that the salts are each capable of releasing at least about 1400 ppm of ions into an aqueous solution having a temperature of about 25° C. and a pH of about 7.0.

In the oral product of this invention, the first and second discrete parts have a pH in water such that a mixed aqueous solution formed by mixing the parts with water and/or saliva has a pH of from about 4.0 to about 10.0, preferably from 4.5 to about 7.0, more preferably from about 5.0 to about 7.0. The pH of the mixed aqueous solution may be controlled by the addition of any acid, base or buffering agent which is safe for use in the oral cavity and which yields the desired pH at the amount employed. Examples of suitable acids are acetic acid, phosphoric acid, hydrochloric acid, citric acid, and malic acid. A particularly suitable base is sodium hydroxide. Suitable buffering agents include, e.g., sodium citrate, sodium benzoate, disodium hydrogen phosphate, sodium dihydrogen phosphate, and the like.

The oral product of this invention contains effective amounts of each of the components therein. With respect to the amounts of the calcium and phosphate salts, the term "effective amount" as used herein means that amount sufficient to effect remineralization of subsurface dental lesions and/or mineralization of exposed dentinal tubules. With respect to the amounts of the fluoride and non-calcium divalent metal salts, the term "effective amount" as used herein means that amount of the respective salts which is effective to enhance the subsurface remineralizing and mineralizing properties of the oral product. With respect to the amount of the sodium gluconate, the term "effective amount" means that amount sufficient to provide the oral product with whitening or stain removal properties. With respect to the anhydrous dicalcium phosphate and the silica abrasive, the term "effective amount" as used herein means those amounts which provide the oral product with improved stain removal properties.

The oral product preferably contains from about 0.05% to about 15.0%, more preferably from about 0.10% to about 10.0%, by weight of the calcium salt(s); from about 0.05% to about 15.0%, more preferably from about 0.10% to about 10.0%, by weight of the orthophosphate salt(s); and from about 0.1% to about 10%, more preferably from about 0.5% to about 3%, by weight of the sodium gluconate. When present, the fluoride salt(s) is preferably used in an amount of from about 0.02% to about 5.0% by weight of the oral product. When present, the non-calcium divalent metal salt is preferably used in an amount of at least about 0.001%, more preferably from about 0.001% to about 2.0%, by weight of the oral product. Furthermore, in preferred embodiments, the oral product contains from about 1% to about 25%, more preferably from about 2% to about 15%, by weight of the anhydrous dicalcium phosphate, and from about 1% to about 25%, more preferably from about 5% to about 15%, by weight of the silica abrasive.

As stated previously herein, the calcium salt component in the oral product of this invention is water-soluble or partially water-soluble. Non-limiting examples of suitable water-soluble calcium salts include calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, calcium valerate, or mixtures of the foregoing.

Non-limiting examples of calcium salts of partial water-solubility suitable for use in this invention include calcium sulfate, anhydrous calcium sulfate, calcium sulfate hemihydrate, calcium sulfate dihydrate, calcium malate, calcium tartrate, calcium malonate, calcium succinate, and mixtures of the foregoing. Calcium sulfate is preferred.

The partially water-soluble calcium salt component of the products of this invention can be prepared in situ, for example, by preparing mixtures of an acid such as, e.g., tartaric acid, and a water-soluble calcium salt such as, e.g., calcium nitrate, and adjusting the pH as needed.

In the present invention, the principle known as the "common ion effect" can be used to control the solubility of the partially water-soluble calcium salt used in the present invention and to optimize calcium release and fluoride stability. To achieve the common ion effect, a salt can be added to the product or solution of this invention wherein the anion of the salt is the same as the anion present in the calcium salt used in the particular product or solution. In the present invention, the sodium, potassium and ammonium salts are preferred for use to achieve the common ion effect. However, an anion which is part of another functional ingredient may also be added. For example, the use of magnesium sulfate in a calcium sulfate-based formulation would supply at least some of the needed sulfate anion.

Preferably, the calcium salt(s) used in the oral product of this invention is calcium sulfate.

Non-limiting examples of suitable orthophosphate salts for use in the present invention include alkali salts and ammonium salts of orthophosphoric acid, such as the mono-, di- or tri- potassium, sodium, and ammonium orthophosphate salts, e.g., monopotassium phosphate, dipotassium phosphate, tripotassium phosphate, monosodium phosphate, disodium phosphate, and trisodium phosphate.

The preferred phosphate salt for use in this invention is monoammonium phosphate.

Suitable fluoride salts include the alkali fluorides, organic fluorides, and water-soluble monofluorophosphates. Examples of suitable alkali fluoride salts include sodium, potassium, lithium, and ammonium fluoride. Metal fluorides such as tin fluoride, indium fluoride, zirconium fluoride, copper fluoride, nickel fluoride, palladium fluoride, fluorozirconates (such as sodium, potassium, and ammonium fluorozirconates), fluorosilicates, fluoroborates, fluorostannites. Suitable organic fluoride salts include, e.g., amine fluorides. Suitable monofluorophosphate salts include, for example, alkali metal monofluorophosphates (e.g., sodium monofluorophosphate, lithium monofluorophosphate, potassium monofluorophosphate), ammonium monofluorophosphate, and aluminum monofluorophosphate.

The preferred fluoride salt is sodium fluoride.

The non-calcium divalent metal salt(s) which can be used in the oral product of this invention may be any water-soluble, non-toxic divalent metal compound which will stabilize the calcium, phosphate and fluoride ions so that these ions do not rapidly or prematurely precipitate before diffusing into the teeth. In practice, however, it has been found that at least one member selected from the group consisting of magnesium, strontium, tin, and zinc, with magnesium being preferred, is the most effective divalent metal in stabilizing the system.

Suitable magnesium compounds include, for example, magnesium acetate, magnesium ammonium sulfate, magnesium benzoate, magnesium bromide, magnesium borate, magnesium citrate, magnesium chloride, magnesium gluconate, magnesium glycerophosphate, magnesium hydroxide, magnesium iodide, magnesium oxide, magnesium propionate, magnesium D-lactate, magnesium DL-lactate, magnesium orthophosphate, magnesium phenolsulfonate, magnesium pyrophosphate, magnesium sulfate, magnesium nitrate, and magnesium tartrate. Preferred magnesium compounds are magnesium chloride, magnesium acetate and magnesium oxide.

Suitable strontium compounds include, for example, strontium acetate, strontium ammonium sulfate, strontium benzoate, strontium bromide, strontium borate, strontium caprylate, strontium carbonate, strontium citrate, strontium chloride, strontium gluconate, strontium glycerophosphate, strontium hydroxide, strontium iodide, strontium oxide, strontium propionate, strontium D-lactate, strontium DL-lactate, strontium pyrophosphate, strontium sulfate, strontium nitrate, and strontium tartrate. Preferred strontium compounds are strontium acetate, strontium chloride, strontium nitrate.

Suitable tin compounds include, for example, stannous acetate, stannous ammonium sulfate, stannous benzoate, stannous bromide, stannous borate, stannous carbonate, stannous citrate, stannous chloride, stannous gluconate, stannous glycerophosphate, stannous hydroxide, stannous iodide, stannous oxide, stannous propionate, stannous D-lactate, stannous DL-lactate, stannous orthophosphate, stannous pyrophosphate, stannous sulfate, stannous nitrate, and stannous tartrate. A preferred tin compound is stannous chloride.

Suitable zinc compounds include, for example, zinc acetate, zinc ammonium sulfate, zinc benzoate, zinc bromide, zinc borate, zinc citrate, zinc chloride, zinc gluconate, zinc glycerophosphate, zinc hydroxide, zinc iodide, zinc oxide, zinc propionate, zinc D-lactate, zinc DL-lactate, zinc pyrophosphate, zinc sulfate, zinc nitrate, and zinc tartrate. Preferred zinc compounds are zinc acetate, zinc chloride, zinc sulfate, and zinc nitrate.

Suitable silica abrasives which can be used in preferred embodiments of the oral product of this invention include, for example, hydrated silica, silica aerogels, fumed silica, precipitated silica, or other finely divided silica. More preferably, the oral product of this invention contains hydrated synthetic amorphous silicas having certain chemical and particle size characteristics especially sorted for the quick release of bioavailable fluoride. The preferred abrasives for use herein are silica gels including the aerogel type silicas, the xerogel type silicas and the Sylodent® type silicas, or combinations thereof which are commercially available from W. R. Grace & Co.

The oral product of this invention can be in the form of a toothpaste, a prophylactic paste, a tooth polish, a gel, a professional gel, a cream, a mouthwash, a rinse, a dental floss, a chewing gum, a lozenge, a tablet, an edible food product, and the like.

Preferably, the oral product of this invention is a toothpaste.

The oral product of this invention may contain one or more conventional additives for dental and oral cosmetics, including but not limited to: surfactants, flavoring agents, sweetening agents, aroma agents, astringents, preservatives (e.g., sodium benzoate, methyl-4-hydroxy benzoate, and the like), sudsing agents, binding agents, humectants, thickening agents (including inorganic thickeners such as hydrated silica), coloring or whitening agents, and the like. When used, these additives are incorporated into the oral product of this invention in amounts which do not substantially adversely affect the properties and characteristics desired of such oral product. The particular amounts of the additives used will depend upon the particular form of the oral product.

Any suitable surface active or detersive material may be included in the oral product of this invention. Such materials are desirable to provide additional detersive, foaming and anti-bacterial properties depending upon the specific type of surface active material. These detergents are usually water-soluble organic compounds and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulfate detergents (e.g., sodium coconut fatty acid monoglyceride monosulfate), higher alkyl sulfate (e.g., sodium lauryl sulfate), alkyl aryl sulfonate (e.g., sodium dodecyl benzene sulfonate), higher fatty acid esters of 1,2-dihydroxy propane sulfonate (e.g., sodium coconut fatty acid ester of 1,2-dihydroxy propane sulfonate), and the like.

The various surface active materials may be used in any suitable amount, generally from about 0.05% to about 10% by weight, and preferably from about 0.5% to about 5% by weight of the oral product.

Suitable flavoring agents include, e.g., oil of wintergreen, oil of peppermint, oil of spearmint, oil of sassafras, oil of clove and any other of the many known flavoring agents or combinations thereof.

Suitable sweetening agents include, e.g., acesulfame, saccharin, dextrose, levulose, sodium cyclamate, and aspartame. Mixtures of sugar with a sweetener, e.g., sucralose, are also contemplated for use in the present invention.

Flavoring and sweetening agents are customarily used in oral dentifrice compositions at levels of from about 0.005% to about 2.0% by weight.

Suitable sudsing agents for use in the present invention include those which are reasonably stable and which form suds throughout the period of application. Preferably, non-soap anionic or nonionic organic synthetic detergents are employed. Examples of such agents include, e.g., water-soluble salts of alkyl sulfate having from 10 to 18 carbon atoms in the alkyl radical, such as sodium lauryl sulfate; water-soluble salts of sulfonated monoglycerides of fatty acids having from 10 to 18 carbon atoms, such as sodium monoglyceride sulfonate; salts of $C_{10}$–$C_{18}$ fatty acid amides of taurine, such as sodium N-methyl taurate; salts of $C_{10}$–$C_{18}$ fatty acid esters of isothionic acid; and substantially saturated aliphatic acyl amides of saturated monoaminocarboxylic acids having 2 to 6 carbon atoms, and in which the acyl radical contains 12 to 16 carbon atoms, such as sodium-N-lauryl sarcoside. Mixtures of two or more sudsing agents can be used.

A binding material can be added to thicken and provide a desirable consistency to the oral product of the present invention. Suitable binding agents include, e.g., water-soluble salts of cellulose ethers, such as, for example, sodium carboxymethyl cellulose, hydroxypropyl cellulose, and hydroxyethyl cellulose. Natural gums such as gum karaya, gum arabic, carrageenan and gum tragacanth, can also be used. A preferred binding agent is xanthan gum alone or in combination with sodium carboxymethyl cellulose. Colloidal magnesium aluminum silicate or finely divided silica can be used as a component of the binding material to further improve the composition's texture. Binding agents in an amount of from about 0.5% to about 5.0% by weight of the oral product of this invention can be used.

It is also desirable to include some humectant material in the oral products of this invention to keep such products from hardening upon exposure to air. Suitable humectants include, e.g., glycerine, sorbitol, xylitol, polyethylene glycol, propylene glycol, and other edible polyhydric alcohols, as well as mixtures thereof. On a pure humectant basis, the concentration of humectant, if present, preferably ranges from about 15% to about 70%, more preferably from about 30% to about 65%, by weight of the oral product.

It is also possible to manufacture the oral product of the present invention in the form of a transparent or translucent gel. This is accomplished by matching the refractive index of the water-humectant system with the abrasives and inorganic thickeners if used.

Professional gels can be formulated similar to dentifrices but with higher fluoride contents. Since these products are not designed for cleaning but only as a fluoride application, abrasives and other cleaning agents need not be included in the formulation.

Other products within the scope of this invention include mouthwashes and rinses. Mouthwashes and rinses generally contain an aqueous solution of ethyl alcohol and flavoring materials. The alcohol provides an antibacterial effect, solubilizes the flavoring materials and provides a pleasant mouth feeling. Alcohol-free mouthwashes are now, however, gaining in popularity. Optionally, mouthwashes and rinses also contain additional antibacterial agents and humectants such as glycerine and sorbitol which give a moist feeling to the mouth.

In addition to the anionic and cationic active ingredients discussed previously herein, mouthwashes and rinses preferably contain from about 0 to about 30%, preferably from about 0 to about 20%, by weight of ethyl alcohol; from about 30% to about 90% by weight of water; from about 0 to about 20% by weight of glycerine or other humectant; from about 0 to about 0.1% by weight of an antibacterial agent; from about 0 to about 0.2% by weight of a soluble fluoride source; from about 0.01% to about 0.5% by weight of a sweetening agent; from about 0.01% to about 2.0% by weight of a flavoring agent; and from about 0.1% to about 1% by weight of an emulsifier-surfactant.

Chewable tablets may be formulated in a manner similar to the aforementioned dentifrices. Since the tablets are packaged in a water-free state, the cationic and anionic parts can be safely included in the same tablet. The reaction between the cationic and anionic parts will begin after they are in contact with the saliva through the chewing action. Chewable tablets are generally formulated without fluoride to avoid potential issues of toxicity.

A chewing gum may also be formulated containing the system covered by this invention. Such a product would normally be formulated without fluoride. In addition to conventional ingredients, the chewing gum would contain a calcium salt, a phosphate salt, and a gluconate salt. The calcium salt is prevented from reacting with the phosphate salt by reducing the pH, reducing the moisture content, encapsulation or by other suitable means.

With respect to toothpastes, gels, creams and the like within the scope of this invention, a plurality of packaging methods may be employed in order to separately contain or store the cationic and anionic parts and provide effective dispensing thereof into the oral cavity.

Thus, the cationic and anionic parts may be simultaneously dispensed from separate collapsible tubes preferably made of plastic, a plastic and metal laminate, etc. For convenience and in order to aid in dispensing substantially equal amounts of the parts, the tubes may be held together by banding or cementing, preferably along the corresponding ventral sides of the tubes.

In another embodiment, the two tubes may be constructed to have abutting, preferably flat, sidewall portions. In the foregoing embodiments, the mouths of the tubes are usually sufficiently close so that sufficient quantities of the cationic and anionic parts of the toothpaste or gel may be simultaneously dispensed directly on the toothbrush with the tubes being capped separately.

Alternatively, another packaging method involves loading the cationic and anionic parts of the paste or gel into separate compartments of the same collapsible composite tube, joined by a common orifice. Such composite tube has compartments separated by a divider which is firmly attached along substantially diametrically opposed portions of the sidewall, and corresponding portions of the head structure of the tube. The divider may be glued or welded to the sidewall and head structure of the tube during manufacture of the latter. The divider is preferably provided with a protruding portion which extends into the mouth of the tube until its edge is substantially flush with the rim of the mouth. Thus, a divider forms with the sidewall two separate compartments of substantially the same volume for storage of the cationic and anionic parts, respectively.

In another alternative packaging method, the two tubes are "concentric". An inner tube lies within and parallel with an outer tube. The mouths of the tubes abut at the same point. Protrusions or the like are inserted between the inner and outer tubes so that the component contained in the outer tube can pass through an available space between the mouth of the outer tube and the mouth of the inner tube. The closures of this tube-within-a-tube (which can screw on the outer tube or simply be held by pressure) may, but does not have to be, equipped with an interior protrusion to fit in the inner tube in order to prevent premature intermixing of the two components at the mouth of the tube.

The tubes of all the above embodiments are usually filled from the bottom and are subsequently sealed together by conventional techniques.

Another alternative packaging arrangement is a pressurized container which is provided with two compartments and two spouts. The internal pressure of the compartments is maintained by a pressurized gas, i.e., nitrogen, at the bottom of each compartment. Operation of a mechanical actuator actuates valves which release the contents of the compartments through the spouts, causing discharge of the paste or gel components onto a brush.

The mouthwash, rinse or similar liquid embodiments are maintained in a manner similar to the pastes or gels in that, during storage, each of the cationic and anionic parts are maintained separate from one another to prevent premature reaction. Upon dispensing, the cationic and anionic parts mix and react in the oral cavity to effect remineralization of dental enamel. The liquid cationic and anionic parts can therefore be stored each in separate compartments of a dual-compartment dispenser. The dispenser usually includes a closure system containing, for example, an inclined crown portion, at least two pouring spouts extending upwardly from an upper surface of the crown portion, and a cover for securement to the crown portion. The cover is provided with closure means, for example, depending plugs, to close the closure. Each pouring spout is preferably provided with a vent opening in addition to product orifices in the spouts. The orifices can be positioned close together on the crown, all of which assists in achieving control over pouring. Transparent containers have proven to be the most satisfactory. Transparency aids a person's ability to accurately and controllably dispense relatively equal volumes from a dual-compartment dispenser. Transparent walled containers also serve a window function for gauging the amounts of liquid remaining in the dispenser. The walls of the containers can be scribed or otherwise calibrated to assist in dispensing the correct remineralizing amount of the mixed aqueous composition.

As mentioned previously herein, in the oral product of this invention, the cationic and anionic parts are kept separate from one another until the product is to be used. Separation of the two parts can be achieved by various ways.

For instance, the cationic and anionic parts may be separated by a physical barrier such as, for example, when the two parts are disposed in separate compartments of a two-compartment container, e.g., two-compartment tube or two-compartment aerosol can. In this embodiment, the two parts are kept separate from one another during storage but are preferably dispensed simultaneously with one another from the container.

The cationic and anionic parts of the product of this invention may also be kept separate from each other by disposing the parts as separate layers in a multilayer product, for example, a two-layer mouthwash, a two-layer chewing gum, and the like.

It is also possible to employ an emulsion or dispersion wherein the cationic part and the anionic part are present in different phases.

It is further possible to provide the cationic part, the anionic part or both parts with a coating (that is to say, encapsulate it), this coating being such as only to release the active substance through the action of heat or through mechanical action. Examples of suitable encapsulation materials include, e.g., shellac; waxes; fats; vinylpyridine; alkyl vinylpyridine and polymers/copolymers of other vinyl monomers; ethyl cellulose, benzyl cellulose, cellulose acetobutyrate and other cellulose derivatives; polyvinyl acetal diethylaminoacetate and dimethylaminoethyl methacrylate/methyl methacrylate copolymers; and the like.

In addition, separation of the cationic and anionic parts may be achieved by disposing one part in an aqueous medium and the other part in a non-aqueous, water-insoluble medium, wherein the aqueous medium and the water-insoluble mediums are capable of simultaneously releasing the cationic and anionic parts. Examples of suitable non-aqueous mediums include non-aqueous solvents such as, e.g., ethyl alcohol, glycerine, propylene glycol and polyethylene oxide. Preferably, the non-aqueous, hydrophilic liquid carrier medium is a polyethylene oxide having a molecular weight of about 400 (also known under the designation "Carbowax 400").

Separation may also be achieved by disposing the two parts in a single carrier medium, wherein the single carrier medium is non-aqueous and hydrophilic and capable of simultaneously releasing the two parts upon contact with water.

Yet another way to separate the cationic and anionic parts is to dispose the cationic part in a first carrier medium and the anionic part in a second carrier medium, wherein the first carrier medium is composed of a material in which the anionic part is insoluble but the cationic part is soluble, further wherein the second carrier medium is composed of a material in which the cationic part is insoluble but the anionic part is soluble.

In the product of this invention, the cationic and anionic parts may both be aqueous, e.g., may both be in the form of aqueous solutions. Alternatively, one or both of the cationic and anionic parts may be non-aqueous. While completely aqueous compositions are preferred in the present invention for application to the teeth, non-aqueous solvents may be employed in combination with water and/or saliva to form an aqueous/non-aqueous medium. Suitable non-aqueous solvents include, e.g., ethyl alcohol, glycerine, propylene glycol and polyethylene oxide. Solvent systems suitable for use in the present invention are those which are safe for use in the mouth.

EXPERIMENTAL

In the Examples and Tables hereinbelow, the following terms have the meanings set forth below:

"pbw"—parts by weight

"CMC 7MF"—sodium carboxymethyl cellulose (7MF, Hercules)

"Abrasive Hydrated Silica I"—Silica gel available under the designation "Sylodent 700®"

"Abrasive Hydrated Silica II"—Silica gel available under the designation "Sylodent 756®"

"Abrasive Hydrated Silica III"—Silica gel available under the designation "Sylodent 767®"

"TISAB"—Total Ionic Solution Adjustment Buffer, which is a buffer solution composed of sodium acetate, sodium chloride, acetic acid, and 1,2-cyclohexane diaminetetraacetic acid

INVENTION EXAMPLE 1 AND CONTROL EXAMPLES A AND B

In Invention Example 1 and Control Examples A and B, the fluoride uptake and enamel solubility reduction properties of three toothpaste products were tested. The Example 1 product is within the scope of the present invention, while the products used in Examples A and B are outside the scope of the present invention.

The toothpaste formulations used in Examples 1 and A are set forth in Table I below. The Example A toothpaste contained the same ingredients as the Example 1 toothpaste except for the sodium fluoride which was replaced with an equivalent amount of distilled water.

In Example B, a USP standard toothpaste containing sodium fluoride and silica was used.

TABLE I

Examples 1 and A: Formulations

| Ingredients | Concentration (pbw) | |
| --- | --- | --- |
| | Ex. 1 | Ex. A |
| Part (A) | | |
| Glycerin | 9.25 | 9.25 |
| Methyl Paraben | 0.025 | 0.025 |
| Propyl Paraben | 0.025 | 0.025 |
| CMC 7MF | 0.225 | 0.225 |
| Xanthan Gum | 0.65 | 0.65 |
| Distilled Water | 16.35 | 16.35 |
| Sorbitol | 7.5 | 7.5 |
| Titanium Dioxide | 0.1 | 0.1 |
| Sodium Saccharin | 0.3 | 0.3 |
| Magnesium Chloride | 0.2 | 0.2 |
| Ammonium Chloride | 0.375 | 0.375 |
| Calcium Sulfate | 1 | 1 |
| Hydrated Silica Thickener | 2.5 | 2.5 |
| Anhydrous Calcium Phosphate | 10 | 10 |
| Sodium Lauryl Sulfate | 0.5 | 0.5 |
| Flavor | 0.5 | 0.5 |
| PEG 40 Hydrogenated Castor Oil | 0.5 | 0.5 |
| TOTAL | 50.00 | 50.00 |
| Part (B) | | |
| Glycerin | 7.5 | 7.5 |
| Methyl Paraben | 0.025 | 0.025 |
| Propyl Paraben | 0.025 | 0.025 |
| CMC 7MF | 0.225 | 0.225 |
| Xanthan Gum | 0.65 | 0.65 |
| Distilled Water | 16.2415 | 16.4915 |
| Sorbitol | 7.5 | 7.5 |
| Titanium Dioxide | 0.1 | 0.1 |
| Sodium Gluconate | 2 | 2 |
| Sodium Saccharin | 0.3 | 0.3 |
| Sodium Fluoride | 0.25 | 0 |
| FD&C Blue #1 | 0.017 | 0.017 |
| Monoammonium Phosphate | 1.1 | 1.1 |
| Phosphoric Acid | 0.0665 | 0.0665 |
| Hydrated Silica Thickener | 2.5 | 2.5 |
| Abrasive Hydrated Silica III | 10 | 10 |
| Sodium Lauryl Sulfate | 0.5 | 0.5 |
| Flavor | 0.5 | 0.5 |
| PEG 40 Hydrogenated Castor Oil | 0.5 | 0.5 |
| TOTAL | 50.00 | 50.00 |

The fluoride uptake properties of the toothpaste products of Examples 1, A and B were measured using the procedure set forth below.

Fluoride Uptake Test Procedure

Three enamel specimens (one specimen per example) were prepared from sound upper human incisors and embedded in an autopolymerizing methacrylate resin so that only the enamel surfaces were exposed. The exposed enamel surfaces were then polished using a 600 grit wet/dry paper and micro-fine alumina.

Each enamel specimen was then etched by immersion into a first etching solution, specifically a 0.5 milliliter of perchloric acid, for 15 seconds.

A 0.25 ml aliquot of the first etching solution was buffered with 0.5 ml of TISAB and 0.25 ml of 1N NaOH. The fluoride content of the buffered etching solution was measured using a fluoride sensitive electrode. This fluoride value is referred to herein as the "pre-treatment fluoride content".

The etched enamel specimens were then reground and polished. Next, an incipient lesion was formed in each of the reground, polished enamel specimens by soaking each specimen in 0.025 M lactic acid containing 0.2 mM of disodium dihydrogen methanehydroxy diphosphonate for 24 hours at room temperature. The lesioned-enamel specimens were then rinsed and stored in a humid environment until use.

In each of Examples 1, A and B, a slurry containing 1 part test product to 3 parts pooled human saliva was prepared. Each enamel specimen was immersed, with stirring, for 30 minutes in a 25-ml aliquot of the corresponding test product slurry (one specimen per slurry) and then rinsed in distilled water.

Next, each specimen was etched by immersion in a second etching solution, specifically 0.5 ml of 1M perchloric acid, for 15 seconds. The fluoride content of the second etching solution was then measured using a fluoride sensitive electrode. This fluoride value is referred to herein as the "post-treatment fluoride content".

For each example, the "post-treatment fluoride content" value was subtracted from the the "pre-treatment fluoride content" value to provide a "fluoride uptake value". The fluoride uptake values, which are expressed as parts per million ("ppm"), obtained in Examples 1, A and B are set forth in Table II below:

TABLE II

Examples 1, A and B: Fluoride Uptake and Enamel Solubility Reduction Results

| Example No. | Fluoride Uptake (ppm) |
| --- | --- |
| 1 | 3401 ± 143 |
| A | 28 ± 4 |
| B | 1375 ± 55 |

The results set forth in Table II show that a toothpaste formulation within the scope of the present invention (Example 1) provided significantly greater fluoride uptake than did either of the toothpaste formulations used in Control Examples A and B. In particular, the fluoride uptake results in Table II show that the Example 1 toothpaste formulation, which contained 2% by weight of sodium gluconate, had much better fluoride uptake properties than did the Example B toothpaste formulation, which contained no sodium gluconate.

The enamel solubility reduction properties of the toothpaste products of Examples 1, A and B were measured using the procedure set forth below.

Enamel Solubility Reduction Test Procedure

In each of Examples 1, A and B, a set of three sound human molars were placed in a disc of red boxing wax, leaving only the enamel exposed. The molars were cleaned and polished to remove deposits and stains, and then "deprotected" to remove residual fluoride by etching the molars in 100 ml of 0.1M lactic acid buffer (pH of 4.5) for two 1-hour periods, followed by rinsing in distilled water. The etched molars were then exposed to 40 ml of buffered lactic acid for 15 minutes at 37° C. Next, the lactic acid buffer was analyzed for phosphate content, this phosphate content being referred to herein as "the pre-treatment phosphate content".

Then, for each of the examples, a slurry containing 15 grams test product to 45 ml water was prepared. Each molar was treated for five minutes with a 40-ml aliquot of the corresponding test product slurry and then rinsed with distilled water. Next, the molars were etched in a 40-ml aliquot of 0.1M of lactic acid buffer (pH of 4.5) for 15 minutes at 37° C., after which the lactic acid buffer was analyzed for phosphate content, this phosphate content being referred to herein as "the post-treatment phosphate content".

The enamel solubility reduction values were calculated using the following equation:

$$ESR = \frac{(P_b - P_a)(100)}{P_b}$$

wherein "ESR" represents the enamel solubility reduction, "$P_b$" represents the pre-treatment phosphate content, and "$P_a$" represents the post-treatment phosphate content.

The enamel solubility reduction values obtained in Examples 1, A and C are set forth in Table III hereinbelow.

TABLE III

Examples 1, A and B: Enamel Solubility Reduction

| Example No. | Enamel Solubility Reduction Value (%) |
|---|---|
| 1 | 24.7 ± 1.5 |
| A | 0.1 ± 1.9 |
| B | 18.6 ± 1.1 |

The results presented in Table III show that molars treated with the toothpaste formulation of the present invention were more resistant to acidic challenges than were the molars treated with the conventional toothpaste of Control Example B. Thus, the results set forth in Table III show that even in the presence of sodium gluconate, the toothpaste of the present invention provides superior fluoride uptake and greater enamel solubility reduction than the conventional toothpaste. The Table III results further show that the toothpaste formulation within the scope of the instant invention also exhibited much better enamel solubility reduction properties than the toothpaste formulation of Example A, which was identical to the Example 1 toothpaste except for the presence of sodium fluoride.

INVENTION EXAMPLE 2 AND CONTROL EXAMPLE C

In Invention Example 2 and Control Example C, two toothpaste products were prepared having the formulations set forth in Table IV.

TABLE IV

Examples 2 and C: Formulations

| Ingredients | Concentration (pbw) | |
|---|---|---|
| | Ex. 2 | Ex. C |
| Part (A) | | |
| Glycerin | 9.25 | 9.25 |
| Methyl Paraben | 0.025 | 0.025 |
| Propyl Paraben | 0.025 | 0.025 |
| CMC 7MF | 0.225 | 0.225 |
| Xanthan Gum | 0.55 | 0.55 |
| Distilled Water | 14.45 | 14.45 |
| Sorbitol | 7.5 | 7.5 |
| Titanium Dioxide | 0.1 | 0.1 |
| Sodium Saccharin | 0.3 | 0.3 |
| Magnesium Chloride | 0.2 | 0.2 |
| Ammonium Chloride | 0.375 | 0.375 |
| Calcium Sulfate | 1 | 1 |
| Hydrated Silica Thickener | 2.0 | 2.0 |
| Abrasive Hydrated Silica I | 5.0 | 5.0 |
| Abrasive Hydrated Silica II | 7.5 | 7.5 |
| Sodium Lauryl Sulfate | 0.5 | 0.5 |
| Flavor | 0.5 | 0.5 |
| PEG 40 Hydrogenated Castor Oil | 0.5 | 0.5 |
| TOTAL | 50.00 | 50.00 |
| Part (B) | | |
| Glycerin | 7.5 | 7.5 |
| Methyl Paraben | 0.025 | 0.025 |
| Propyl Paraben | 0.025 | 0.025 |
| CMC 7MF | 0.225 | 0.225 |
| Xanthan Gum | 0.65 | 0.65 |
| Distilled Water | 14.808 | 15.808 |
| Sorbitol | 7.5 | 7.5 |
| Titanium Dioxide | 0.1 | 0.1 |
| Sodium Gluconate | 1 | 0 |
| Sodium Saccharin | 0.3 | 0.3 |
| Sodium Fluoride | 0.25 | 0.25 |
| FD&C Blue #1 | 0.017 | 0.017 |
| Monoammonium Phosphate | 1.1 | 1.1 |
| Phosphoric Acid | 1 | 1 |
| Hydrated Silica Thickener 165 | 1.5 | 1.5 |
| Abrasive Hydrated Silica I | 5 | 5 |
| Abrasive Hydrated Silica II | 7.5 | 7.5 |
| Sodium Lauryl Sulfate | 0.5 | 0.5 |
| Flavor | 0.5 | 0.5 |
| PEG 40 Hydrogenated Castor Oil | 0.5 | 0.5 |
| TOTAL | 50.00 | 50.00 |

The pellicle (i.e., stain) removal properties of the toothpaste formulations of Examples 2 and C were determined using the following procedure.

Pellicle Removal Test Procedure

Bovine, permanent, central incisors were cut to obtain two enamel specimens each having dimensions of about 10×10 millimeters. Each specimen was embedded in an autopolymerizing methacrylate resin so that only the enamel surfaces were exposed. The enamel surfaces were then smoothed and polished on a lapidary wheel and lightly etched to expedite stain accumulation and adherence.

The specimens were then placed on a rotating rod in a 37° C. incubator, wherein the specimens were alternately exposed to air and a solution (the "staining broth") containing trypticase soy broth, tea, coffee, mucin, $FeCl_3$, and *Sarcina lutea*.

The staining broth was changed and the specimens rinsed twice daily for four days. After the four days, a darkly-stained pellicle film was apparent on the enamel surfaces of the specimens. The specimens were rinsed, allowed to air dry, and refrigerated until use.

The enamel specimens were then mounted on a mechanical V-8 cross-brushing machine equipped with soft nylon filament (Oral-B 40) toothbrushes. Tension on each enamel surface was adjusted to 150 grams.

Two slurries were prepared from the toothpaste products used in Examples 2 and C (one slurry per toothpaste product). Each slurry was made by mixing 25 grams of the toothpaste with 40 milliliters of deionized water. Each specimen was brushed for 800 strokes for 4.5 minutes with a corresponding slurry (one slurry per specimen). After brushing, the specimens were rinsed and blotted dry.

The extent of pellicle removal effected by the two slurries in Examples 2 and C was determined by comparing the "whiteness" value of the specimens cleaned by the two slurries with an arbitrary "whiteness" value of 100 assigned to a whitening standard. The "whiteness" value was determined photometrically with a Minolta C221 calorimeter, using only the "L*" value of the CIE (Commission International D'Eclairage) L*, a* and b* scale. The L* value is a measure of response to the eye to lightness and darkness. The higher the L* value, the whiter the teeth appear.

Thus, the higher the "whiteness" value (up to 100), the more pellicle that was removed.

The "whiteness" values obtained with the slurries used in Examples 2 and C are set forth in Table V below.

TABLE V

Examples 2 and C: Stain Removal Properties

| Example No. | Stain Removal (weight %) |
| --- | --- |
| 2 | 96 |
| C | 84 |

The data set forth in Table V shows that the toothpaste formulation of Example 2, which is within the scope of the instant invention, containing 1% sodium gluconate, removed more pellicle than did the toothpaste formulation of Control Example C, which contained the same abrasive system as the Example 1 toothpaste but which contained no sodium gluconate.

INVENTION EXAMPLES 3 AND 4

In Invention Examples 3 and 4, two toothpaste products were prepared having the formulations set forth in Table VI below.

TABLE VI

Examples 3 and 4: Formulations

| | Concentration (pbw) | |
| --- | --- | --- |
| Ingredients | Ex. 3 | Ex. 4 |
| Part (A) | | |
| Glycerin | 9.25 | 9.25 |
| Methyl Paraben | 0.025 | 0.025 |
| Propyl Paraben | 0.025 | 0.025 |
| CMC 7MF | 0.225 | 0.225 |
| Xanthan Gum | 0.65 | 0.65 |
| Distilled Water | 16.85 | 17.35 |
| Sorbitol | 7.5 | 7.5 |
| Titanium Dioxide | 0.1 | 0.1 |
| Sodium Saccharin | 0.3 | 0.3 |
| Magnesium Chloride | 0.2 | 0.2 |
| Ammonium Chloride | 0.375 | 0.375 |
| Calcium Sulfate | 1 | 1 |
| Hydrated Silica Thickener 165 | 2.25 | 1.75 |
| Abrasive Hydrated Silica III | 7.5 | 7.5 |
| Anhydrous Calcium Phosphate | 2.5 | 2.5 |
| Sodium Lauryl Sulfate | 0.25 | 0.25 |
| Flavor | 0.5 | 0.5 |
| PEG 40 Hydrogenated Castor Oil | 0.5 | 0.5 |
| TOTAL | 50.00 | 50.00 |
| Part (B) | | |
| Glycerin | 7.5 | 7.5 |
| Methyl Paraben | 0.025 | 0.025 |
| Propyl Paraben | 0.025 | 0.025 |
| CNC 7MF | 0.225 | 0.225 |
| Xanthan Gum | 0.65 | 0.65 |
| Distilled Water | 17.808 | 17.308 |
| Sorbitol | 7.5 | 7.5 |
| Titanium Dioxide | 0.1 | 0.1 |
| Sodium Gluconate | 1 | 2 |

TABLE VI-continued

Examples 3 and 4: Formulations

| | Concentration (pbw) | |
| --- | --- | --- |
| Ingredients | Ex. 3 | Ex. 4 |
| Sodium Saccharin | 0.3 | 0.3 |
| Sodium Fluoride | 0.25 | 0.25 |
| FD&C Blue #1 | 0.017 | 0.017 |
| Nonoammonium Phosphate | 1.1 | 1.1 |
| Hydrated Silica Thickener 165 | 2.0 | 1.5 |
| Abrasive Hydrated Silica I | 2.5 | 2.5 |
| Abrasive Hydrated Silica III | 7.5 | 7.5 |
| Sodium Lauryl Sulfate | 0.5 | 0.5 |
| Flavor | 0.5 | 0.5 |
| PEG 40 Hydrogenated Castor Oil | 0.5 | 0.5 |
| TOTAL | 50.00 | 50.00 |

The pellicle (i.e., stain) removal properties of the toothpaste formulations of Examples 3 and 4 were determined using the same procedure followed in Examples 2 and C above. The results are set forth in Table VII below:

TABLE VII

Examples 3 and 4: Stain Removal Properties

| Example No. | Stain Removal (weight %) |
| --- | --- |
| 3 | 65 |
| 4 | 77 |

The data set forth in Table VII shows that the toothpaste formulation of Example 4, containing 2% sodium gluconate, provided greater stain removal than the toothpaste formulation of Example 3, which contained the same abrasive system as the Example 4 toothpaste but which contained only 1.0% sodium gluconate.

What is claimed is:

1. An oral product effective for remineralizing subsurface dental lesions, mineralizing exposed dentinal tubules and whitening teeth stained with discoloring residues containing heavy metal ions, comprising:

(A) a first discrete part comprising an effective amount of at least one water-soluble or partially water-soluble calcium salt, and (B) a second discrete part comprising an effective amount of at least one water-soluble orthophosphate salt and an effective amount of sodium gluconate; wherein parts (A) and (B) have a pH in water such that a mixed aqueous solution formed by mixing parts (A) and (B) with water and/or saliva has a pH of from about 4.0 to about 10.0.

2. A product according to claim 1, wherein the product comprises from about 0.05% to about 15.0% by weight of the calcium salt, from about 0.05% to about 15.0% by weight of the orthophosphate salt, and from about 0.1% to about 10% by weight of the sodium gluconate.

3. A product according to claim 1, wherein parts (A) and (B) have a pH in water such that the mixed aqueous solution has a pH of from 4.5 to about 7.0.

4. A product according to claim 1, wherein the calcium salt is a water-soluble calcium salt selected from the group consisting of calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, and calcium valerate.

5. A product according to claim 1, wherein the calcium salt is a partially water-soluble calcium salt selected from the group consisting of calcium sulfate, anhydrous calcium sulfate, calcium sulfate hemihydrate, calcium sulfate dihydrate, calcium malate, calcium tartrate, calcium malonate, calcium succinate, and mixtures of the foregoing.

6. A product according to claim 5, wherein the partially water-soluble calcium salt is calcium sulfate.

7. A product according to claim 1, wherein the orthophosphate salt is selected from the group consisting of alkali metal salts of orthophosphoric acid and ammonium salts of orthophosphoric acid.

8. A product according to claim 1, wherein part (B) further comprises an effective amount of at least one water-soluble fluoride salt.

9. A product according to claim 8, wherein the product comprises from about 0.01% to about 5.0% by weight of the fluoride salt.

10. A product according to claim 8, wherein the fluoride salt is sodium fluoride or sodium monofluorophosphate.

11. A product according to claim 1, wherein part (A) further comprises an effective amount of a non-toxic, non-calcium, water-soluble divalent metal salt.

12. A product according to claim 1, wherein the product is a toothpaste.

13. A product according to claim 1, wherein part (A) further comprises an effective amount of an anhydrous dicalcium phosphate abrasive, and part (B) further comprises an effective amount of a silica abrasive, the effective amounts of the anhydrous dicalcium phosphate abrasive and the silica abrasive are such as to provide the product with improved stain-removing properties.

14. A product according to claim 13, wherein the product comprises from about 1% to about 25% by weight of the anhydrous dicalcium phosphate abrasive and from about 1% to about 25% by weight of the silica abrasive.

15. A product according to claim 13, wherein the silica abrasive is a hydrated amorphous silica.

16. A product according to claim 15, wherein the hydrated amorphous silica is a silica gel.

17. A product according to claim 13, wherein the product is a toothpaste.

18. A product according to claim 13, wherein part (B) further comprises an effective amount of at least one water-soluble fluoride salt.

19. A product according to claim 8, wherein part (A) further comprises an effective amount of a non-toxic, non-calcium, water-soluble divalent metal salt.

20. A product according to claim 19, wherein said non-toxic, non-calcium, water soluble divalent metal salt is a magnesium salt.

* * * * *